US012616425B2

(12) United States Patent
Movva et al.

(10) Patent No.: US 12,616,425 B2
(45) Date of Patent: May 5, 2026

(54) WEARABLE DEVICE HEALTHCARE SYSTEM

(71) Applicant: CarePredict, Inc., Plantation, FL (US)

(72) Inventors: Satish Movva, Davie, FL (US); Srinaag Vitahavya Samudrala, Pompano Beach, FL (US); Babar Farooq Werrich, Davie, FL (US); Christopher Thomas Crocker, Sunrise, FL (US); Katherine Grace Dupey, Fremont, OH (US); Akshay Dalavai, Plantation, FL (US); Gregory Brian Zobel, Murrieta, CA (US)

(73) Assignee: CarePredict, Inc., Plantation, FL (US)

( * ) Notice: Subject to any disclaimer, the term of this patent is extended or adjusted under 35 U.S.C. 154(b) by 507 days.

(21) Appl. No.: 18/147,978

(22) Filed: Dec. 29, 2022

(65) Prior Publication Data

US 2024/0148340 A1 May 9, 2024

Related U.S. Application Data

(60) Provisional application No. 63/382,376, filed on Nov. 4, 2022.

(51) Int. Cl.
| | |
|---|---|
| *A61B 5/00* | (2006.01) |
| *A61B 5/021* | (2006.01) |
| *G16H 40/67* | (2018.01) |

(52) U.S. Cl.
CPC .......... *A61B 5/7405* (2013.01); *A61B 5/6802* (2013.01); *A61B 5/7282* (2013.01); *G16H 40/67* (2018.01); *A61B 5/021* (2013.01)

(58) Field of Classification Search
None
See application file for complete search history.

(56) References Cited

U.S. PATENT DOCUMENTS

| | | | | | |
|---|---|---|---|---|---|
| 5,612,869 | A | * | 3/1997 | Letzt ...................... | G16H 20/10 |
| | | | | | 704/251 |
| 10,251,598 | B2 | * | 4/2019 | Barnes ................. | A61B 5/4812 |
| 10,997,566 | B2 | * | 5/2021 | Barnes ..................... | G06N 5/02 |
| 2011/0070835 | A1 | * | 3/2011 | Borras ................... | G16H 20/00 |
| | | | | | 455/41.2 |
| 2013/0096649 | A1 | * | 4/2013 | Martin ................... | G16H 15/00 |
| | | | | | 607/60 |
| 2017/0293727 | A1 | * | 10/2017 | Klaassen ............... | G16H 40/67 |
| 2017/0323064 | A1 | * | 11/2017 | Bates ..................... | G16H 50/20 |
| 2018/0000414 | A1 | * | 1/2018 | Lowet ............... | A61B 5/02055 |
| 2018/0288024 | A1 | * | 10/2018 | Munafo ................. | G16H 40/67 |

(Continued)

*Primary Examiner* — Carl H Layno
*Assistant Examiner* — Manolis Pahakis
(74) *Attorney, Agent, or Firm* — DLA Piper LLP (US)

(57) ABSTRACT

In some embodiments, a wearable device detects a trigger event. The trigger event indicates a type of measurement to take. Based on the trigger event, the wearable device selects an instruction audio message corresponding to the type of measurement to be taken. The instruction audio message includes instructions for how to conduct the type of measurement. The wearable device connects to an appropriate measuring apparatus based on the type of measurement to be taken and the instruction audio message. The wearable device plays the instruction audio message to a patient of the wearable device. The wearable device receives measurements from the appropriate measuring apparatus.

14 Claims, 9 Drawing Sheets

(56)     References Cited

U.S. PATENT DOCUMENTS

| 2019/0069154 | A1* | 2/2019 | Booth | ..................... | H04W 4/90 |
| 2019/0239775 | A1* | 8/2019 | Movva | ................. | A61B 5/0017 |
| 2021/0068723 | A1* | 3/2021 | Balkan | .................. | G16H 50/30 |
| 2023/0343458 | A1* | 10/2023 | Ahmed | ............... | A61B 5/7282 |
| 2024/0087737 | A1* | 3/2024 | Movva | .................. | G16H 40/67 |

* cited by examiner

Figure 5:
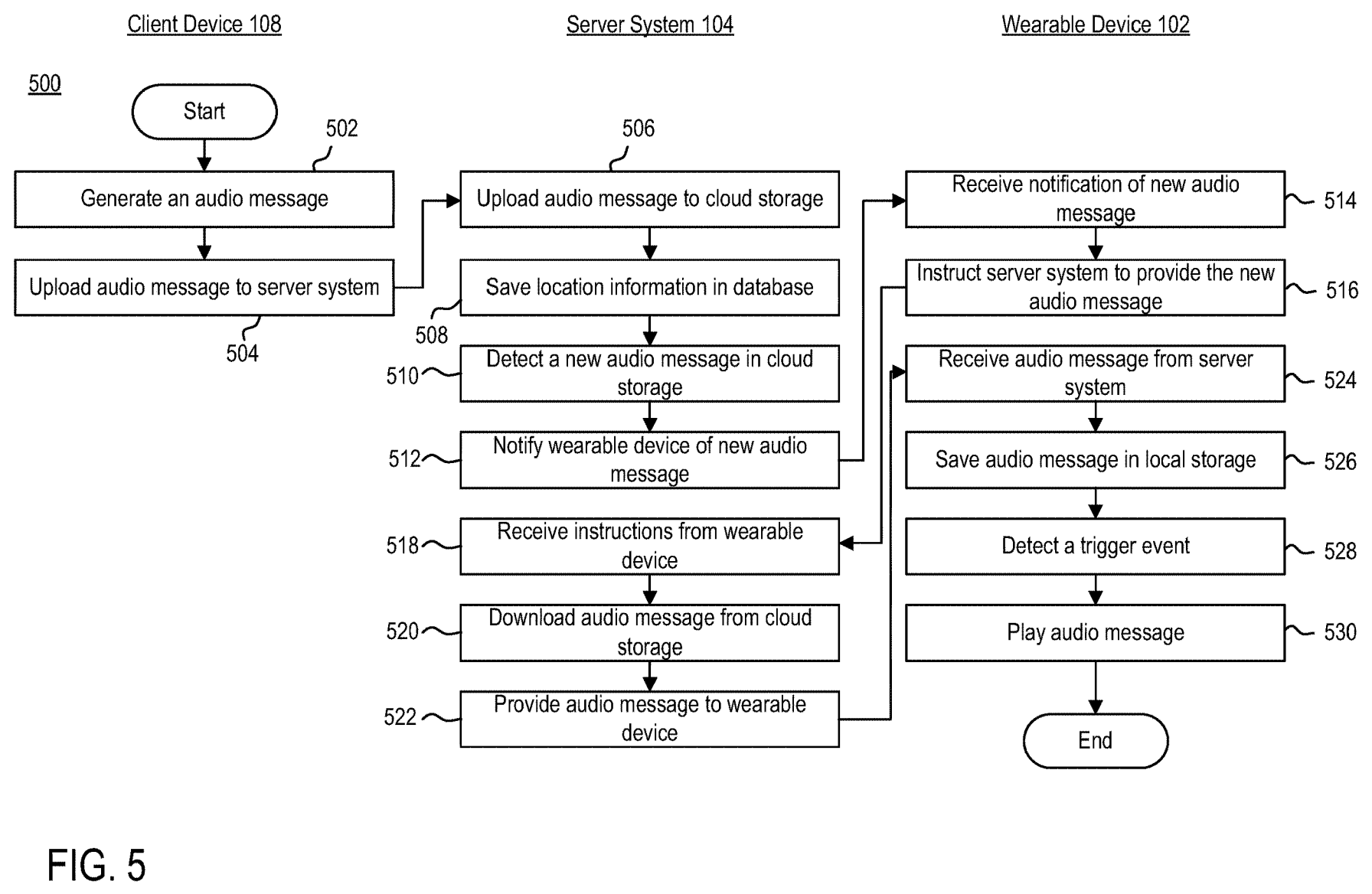

Wearable Device 102

514 — Receive notification of new audio message

516 — Instruct server system to provide the new audio message

524 — Receive audio message from server system

526 — Save audio message in local storage

528 — Detect a trigger event

530 — Play audio message

End

Server System 104

506

Upload audio message to cloud storage

Save location information in database — 508

Detect a new audio message in cloud storage — 510

Notify wearable device of new audio message — 512

Receive instructions from wearable device — 518

Download audio message from cloud storage — 520

Provide audio message to wearable device — 522

Client Device 108

502

Start

Generate an audio message

Upload audio message to server system — 504

Figure 6:
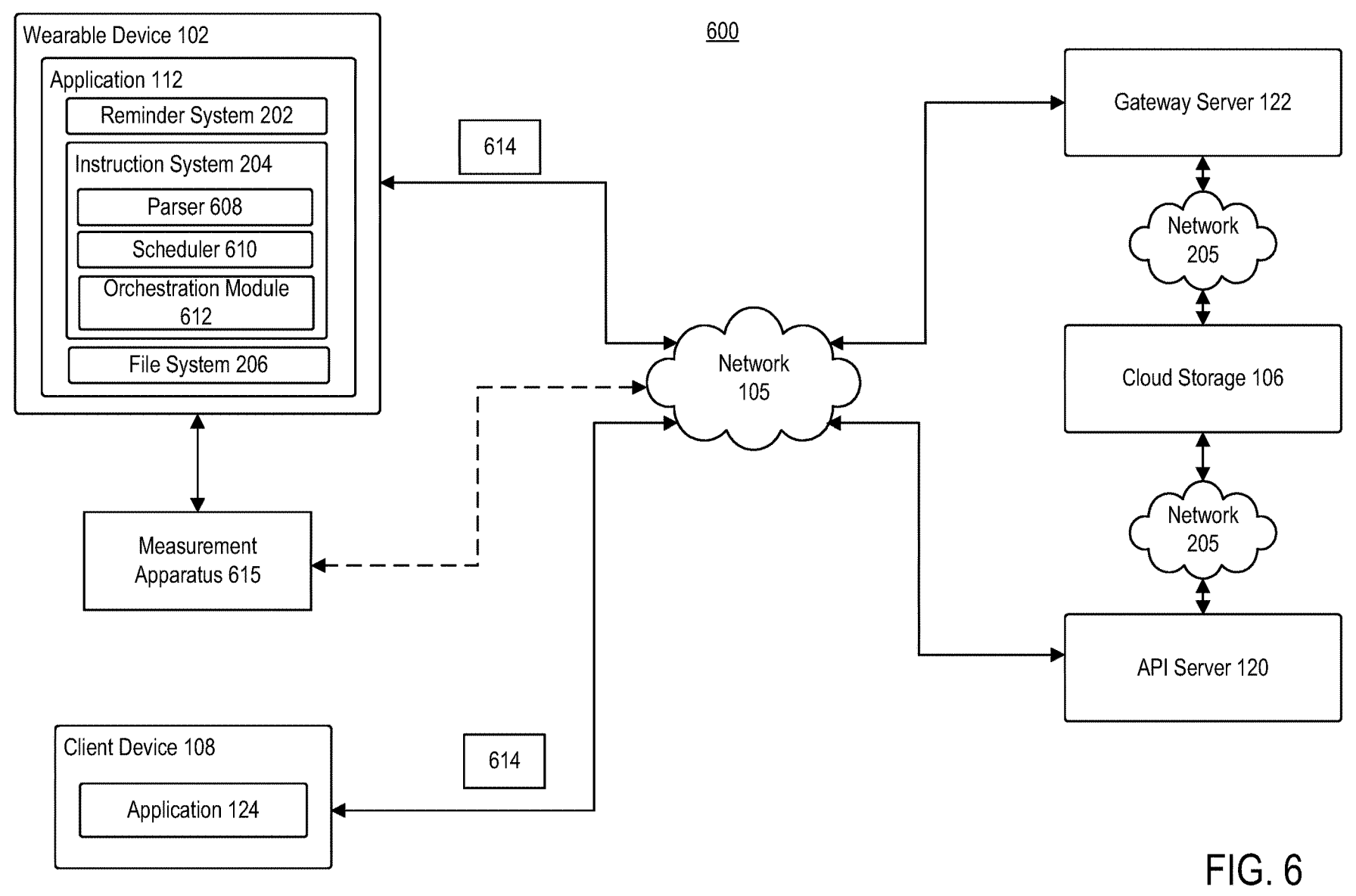

Gateway Server 122

Network 205

Cloud Storage 106

Network 205

API Server 120

Network 105

614

614

Wearable Device 102

Application 112

Reminder System 202

Instruction System 204

Parser 608

Scheduler 610

Orchestration Module 612

File System 206

Measurement Apparatus 615

Client Device 108

Application 124

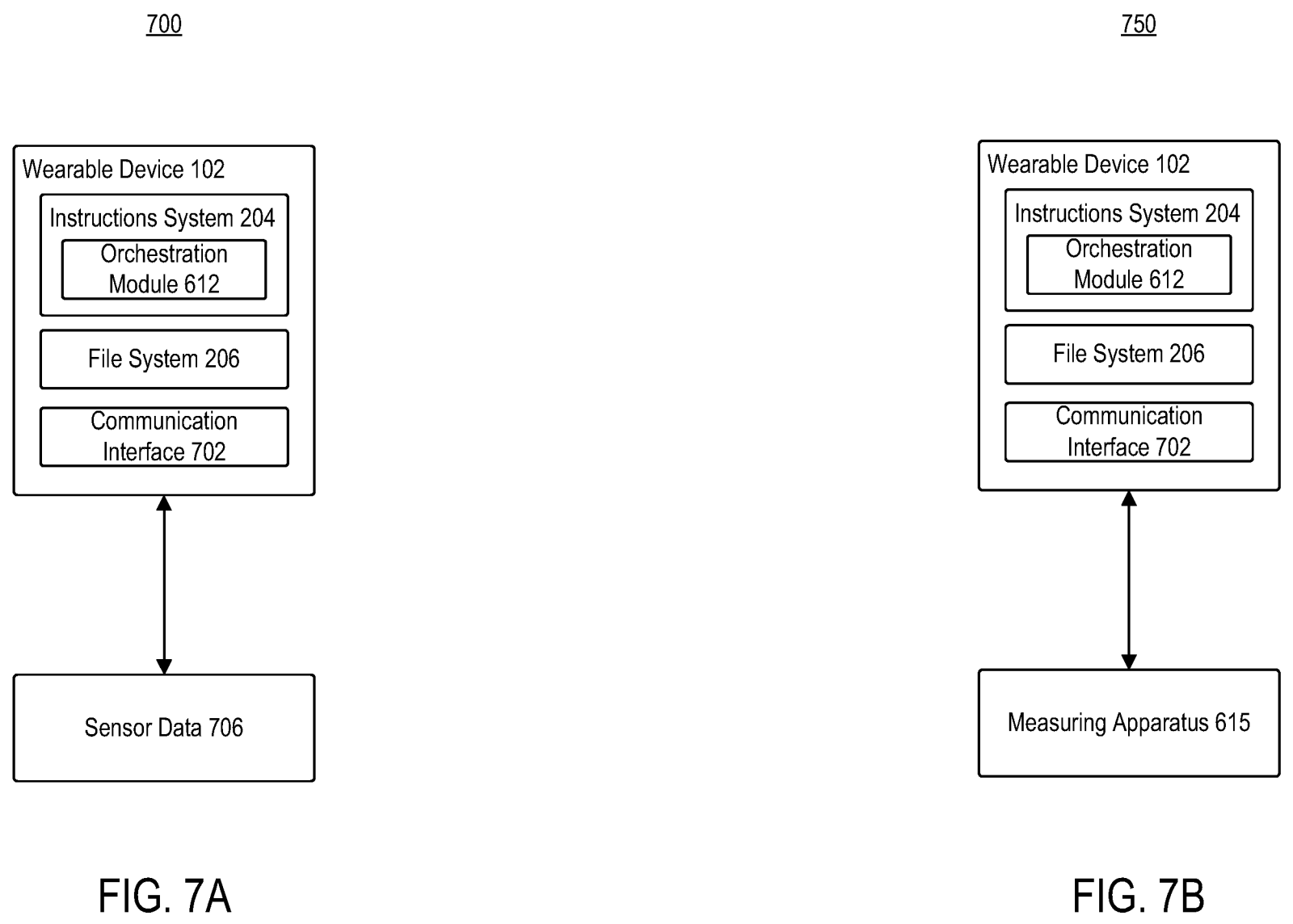

750

Wearable Device 102

Instructions System 204

Orchestration Module 612

File System 206

Communication Interface 702

Measuring Apparatus 615

Wearable Device 102

Instructions System 204

Orchestration Module 612

File System 206

Communication Interface 702

Sensor Data 706

FIG. 7A

WEARABLE DEVICE HEALTHCARE SYSTEM

FIELD OF THE DISCLOSURE

The present disclosure generally relates to a wearable device for use in a healthcare system and, more specifically, a wearable device configured to deliver customized reminders and messages to patients.

BACKGROUND

Wearables are ubiquitous now in personal health. Wearables typically include sensors that include accelerometers, gyros, inclinometers, and magnetometers, among others. Such sensors can detect certain trigger events, such as location-based trigger events, or activities, such as walking, running, sleeping, sitting, falling, and rolling among other functional states of a wearer.

SUMMARY

In some embodiments, a wearable device detects a trigger event. The trigger event indicates a type of measurement to take. Based on the trigger event, the wearable device selects an instruction audio message corresponding to the type of measurement to be taken. The instruction audio message includes instructions for how to conduct the type of measurement. The wearable device connects to an appropriate measuring apparatus based on the type of measurement to be taken and the instruction audio message. The wearable device plays the instruction audio message to a patient of the wearable device. The wearable device receives measurements from the appropriate measuring apparatus.

In some embodiments, a non-transitory computer readable medium is disclosed herein. The non-transitory computer readable medium includes one or more sequences of instructions, which, when executed by one or more processors, causes a wearable device to perform operations. The operations include detecting, by a wearable device, a trigger event. The trigger event indicates a type of measurement to take. The operations further include, based on the trigger event, selecting, by the wearable device, an instruction audio message corresponding to the type of measurement to be taken. The instruction audio message includes instructions for how to conduct the type of measurement. The operations further include connecting, by the wearable device, to an appropriate measuring apparatus based on the type of measurement to be taken and the instruction audio message. The operations further include playing, by the wearable device, the instruction audio message to a patient of the wearable device. The operations further include receiving, by the wearable device, measurements from the appropriate measuring apparatus.

In some embodiments, a system is disclosed herein. The system includes a processor and a memory. The memory has programming instructions stored thereon, which, when executed by the processor, causes the system to perform operations. The operations include detecting a trigger event. The trigger event indicates a type of measurement to take. The operations include, based on the trigger event, selecting an instruction audio message corresponding to the type of measurement to be taken. The instruction audio message includes instructions for how to conduct the type of measurement. The operations include connecting to an appropriate measuring apparatus based on the type of measurement to be taken and the instruction audio message. The operations include playing the instruction audio message to a patient associated with the system. The operations include receiving measurements from the appropriate measuring apparatus.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrated only typical embodiments of this disclosure and are therefore not to be considered limiting of its scope, for the disclosure may admit to other equally effective embodiments.

FIG. 5 is a flow diagram illustrating a method of playing back a reminder audio message to a user of wearable device, according to example embodiments.

FIG. 6 is a block diagram illustrating a computing environment, according to example embodiments.

FIG. 7A is a block diagram illustrating a computing environment, according to example embodiments.

FIG. 7B is a block diagram illustrating a computing environment, according to example embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
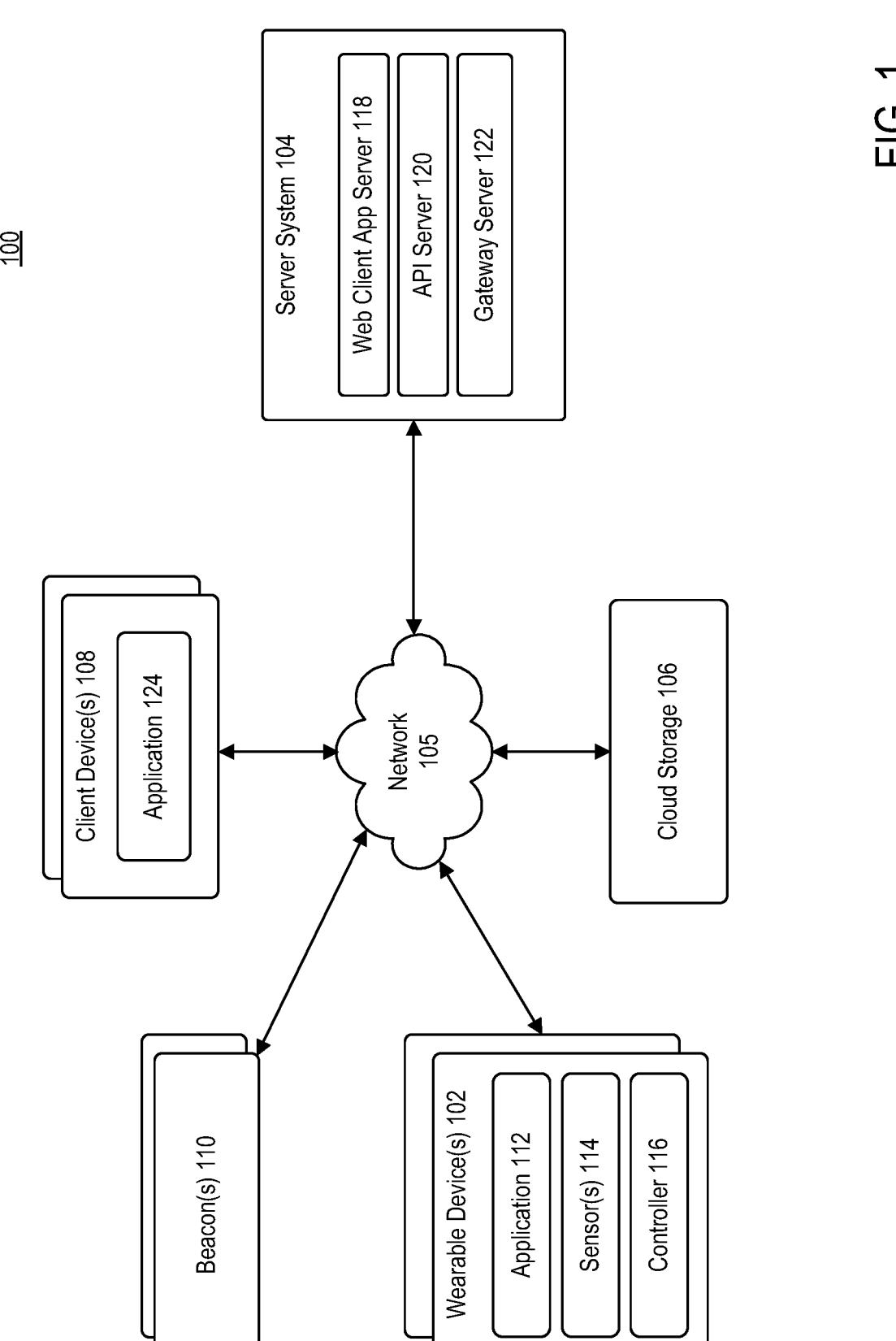
FIG. 1 is a block diagram illustrating a computing environment, according to example embodiments.

As people age, their memory deficits may increase. An aging person typically needs constant reminders for vital health behaviors, as well as for routine everyday tasks. For example, elderly individuals frequently need reminders to take medications, to attend upcoming events and appointments, to perform certain tasks (e.g., check in with family, order groceries, make an appointment with the doctor, etc.), to drink water (dehydration is a leading cause of falls and hospitalizations in elderly men), to eat timely meals, and to be given a health nudge (e.g., reminders to stand, to stretch if too much sitting, to get extra steps in before day ends, or to get more on-feet time to reduce chronic obstructive pulmonary disease (COPD) exacerbation). As memory deficits continue to increase, an aging person needs reminders for basic hygiene tasks of daily living (e.g., to get up from bed, to go to the bathroom, to brush teeth, to get dressed, etc.)

As people age, their social interaction also declines. To avoid the cognitive declines associated with decreased social interaction, an aging person needs stimulation from familiar social contacts to encourage interaction. For example, a familiar voice greeting at the start and end of a day, a familiar voice helping to remember events, names and people, and a familiar voice notifying you of how you compare to people in your social group (e.g., "gamify" wellness—Susie cooked meals for 5 days straight, and you only cooked twice, etc.). In addition, as a person ages, their diminishing interests and abilities are often opaque to them. A familiar voice speaking quantified data can help an aging person be more motivated to engage in their own health and to slow down their age-related declines. For example: "Grandma you used to cook every day and now you are only cooking two days a week—you used to love cooking, can you cook more please?" or "Grandma you used to walk 300 steps every day and now you are only walking 200 steps— please try and get back to 300 steps by the time I come to visit you for thanksgiving."

While reminder-based technology exists, conventional approaches to reminder-based technology with aging individuals is limited. For example, with person-based reminders, such systems are typically subjective, unreliable, and may not be timely. Many aged people need multiple reminders and relying on a person to deliver reminders cannot be provided with consistency. With fixed device systems, such systems are often devices fixed in one location of a home and do not know whether a target person is present in earshot, awake, or aware of when a reminder is played. Such fixed systems are also unable to collect an acknowledgment of receipt of reminder. With existing wearable devices, they often rely on screen-based reminders and/or require an aged person to feel the haptic feedback, look at the screen, and comprehend the small text for a particular reminder. Such small screens often restrict the amount of text in the reminder. Further, the haptic feedback preamble to reminders is often not felt. These conventional device-based systems generally are impersonal and have no emotional or social connection to the aged person to trigger a compliant response.

Further, conventional device-based systems fail to consider a person's current state (e.g., awake, sitting, sleeping, in the bathroom, cooking, etc.) when finding an appropriate time to play the reminder. Such conventional systems also fail to consider a person's current context to adaptively decide to play or not play a reminder, or to play or not play a message based on the occurrence or non-occurrence of a particular event. For example, if a senior is suddenly going to the bathroom too frequently, the senior may be prompted with a message asking whether a family member should be notified. Similarly, if a fall is detected, the senior may be prompted with a message asking whether assistance is required.

Further, conventional device-based systems fail to provide feedback to the person who initiated the reminder. For example, such systems do not provide any information to the person who initiated the reminder regarding whether the reminder was played at the designated time or whether the reminder was not played for some intervening reason (e.g., the senior was detected to be sleeping or the wearable was not powered on, etc.). Conventional systems are further unable to provide a method for the senior to confirm back to the initiator of the reminder that the reminder was heard by the senior.

One or more techniques described herein improve upon conventional systems by delivering context-aware notifications to individuals. In some embodiments, one or more techniques provided herein further deliver confirmation of receipt by the senior back to the initiator of the reminder. For example, the present system may understand or identify the context of the individual (e.g., their room location, their activity state (e.g., sleeping, sitting, standing cooking, etc.), and may deliver notifications to the individual based on their current context. Such system may deliver such reminders to the user using voice notifications with a preamble sound or tone that sensitizes the individual to the message about to follow. Further, one or more techniques provided herein may allow individuals associated with the aging person to record reminders using their own voice to be replayed at any recurrent pattern.

Further, clinical monitoring often consists of measuring certain physiological signals at specific periodic intervals and analyzing the data to identify the current state of a disease condition. For example, a patient with hypertension disease may be monitored for high blood pressure several times a day and as the condition changes, medications and other therapies are modulated to keep the disease in check.

Before the widespread availability of physiological measuring apparatus directly to consumers, such measurements took place in clinical settings: physician offices, hospitals, clinics, emergency rooms and nursing homes.

As patients age and their mobility decreases, it becomes important for the person to take their own measurements at their own places of residence. The availability of measuring apparatus off the shelf and at affordable prices meant that a person can take their own measurements at home and then relay that information to a clinician. However, the process of communicating the measurements timely and accurately has become a challenge, as self-reporting of data is unreliable as patients age.

As a result, a new industry was born, coined Remote Patient Monitoring (RPM), wherein the measurements would be communicated electronically to a clinician for evaluation automatically. The clinician, upon review of the data, would then orchestrate the right intervention if needed.

RPM typically consists of a variety of FDA approved apparatus to measure weight, temperature, blood pressure, glucose or blood sugar, heart rate, pulse oximetry, spirometry to name just a few. These apparatuses may be connected to a computer kiosk of some form that would have a method to communicate electronically to a clinician all the values measured. Such systems could support multiple apparatus to each measure specific signals for as many chronic conditions as need to be managed.

With the advent of mobile devices, modern RPM systems began to use a smart tablet or a smartphone to collect the signals from measuring apparatus via some form of wireless communication.

As RPM has proliferated massively due to the start of reimbursement coverage by healthcare systems (especially in the US through Medicare), some failings have become apparent: patients often fail to take measurements timely; patients often fail to take measurements accurately; and patients are challenged to connect a measuring apparatus with a smart device.

The failings occur because as patients age, they become more cognitively impaired, especially around memory, recall and executive function in performing tasks. Patients may require timely repetition of instructions to successfully perform a task so that they can be guided with specific instructions in taking their measurement consistently each time. Further, using off the shelf devices requires a patient to install specific applications on their smart device and perform the technical process of pairing the measuring device to the smart device. Such process can result in errors as smart devices continue to advance in their technology, thus exceeding the technical proficiency levels of an elderly patient.

Current approaches to remote patient monitoring are limited to a fixed kiosk or a device that is not in immediate proximity to the patient, thus any reminders or guidance becomes improbable. Instead, any reminder function is limited to, at most, a notification on a smart device or on a fixed kiosk. Further, no conventional approach takes into account the patient's state when the notification arrives. For example, the notifications do not account for whether the patient is proximal, asleep, or engaged in an activity that precludes use of a measuring apparatus at that instant. In other words, current approaches fail to take into account a person's current state to find the appropriate time to play the reminder or guidance.

One or more techniques described herein further provide an improvement over conventional system by delivering to patients guidance or instructions for taking their remote measurements. Such guidance or instructions may be delivered to patients via a wearable device, such that the patients are no longer required to be present in a certain room in order to hear the message. By providing patients with instructions via their wearable device, measurement consistency can be achieved. For example, the reminder and instructions can say: "It's time to take your blood pressure. Make sure you are sitting down comfortably, place your arm on the table and relax it, place the cuff with the arrow on your inner elbow, press the silver button on the blood pressure monitor to take the measurement, wait for the beep before moving your arm."

FIG. 1 is a block diagram illustrating a computing environment 100, according to example embodiments. Computing environment 100 may include wearable devices 102, server system 104, cloud storage 106, and client devices 108 communicating via network 105.

Network 105 may be of any suitable type, including individual connections via the Internet, such as cellular or Wi-Fi networks. In some embodiments, network 105 may connect terminals, services, and mobile devices using direct connections, such as radio frequency identification (RFID), near-field communication (NFC), Bluetooth™, low-energy Bluetooth™ (BLE), Wi-Fi™ ZigBee™, ambient backscatter communication (ABC) protocols, Long Range Wide area networks (LoRAWAN), USB, WAN, or LAN. Because the information transmitted may be personal or confidential, security concerns may dictate one or more of these types of connection be encrypted or otherwise secured. In some embodiments, however, the information being transmitted may be less personal, and therefore, the network connections may be selected for convenience over security.

Network 105 may include any type of computer networking arrangement used to exchange data or information. For example, network 105 may be the Internet, a private data network, virtual private network using a public network and/or other suitable connection(s) that enables components in computing environment 100 to send and receive information between the components of environment 100.

Wearable device 102 may be representative of an electronic device that is worn by a user. For example, wearable device 102 may be representative of an electronic device having a microcontroller or microprocessor. In some embodiments, wearable device 102 may be representative of any wearable device to be worn by the user that may be configured to deliver voice-based notifications to the wearer.

As shown, wearable device 102 may include application 112, one or more sensors 114, and a controller 116. Application 112 may be representative of a health notification application associated with server system 104. In some embodiments, application 112 may be a standalone application associated with server system 104. Wearable device 102 may communicate over network 105 to request or receive audio messages from web client application server 118 of server system 104. For example, wearable device 102 may communicate with web client application server 118 over network 105 to receive an audio message to be played to a wearer of wearable device 102 at a predefined time period. In some embodiments, audio message may be representative of a customized voice message generated by the user of client device 108. In some embodiments, audio message may be representative of a sound, tone, or other notification that alerts the wearer of wearable device 102.

Sensors 114 may be representative of one or more sensors associated with wearable device 102. Some non-exhaustive list of sensors may include, but are not limited to, humidity sensors, pressure sensors, ambient temperature sensors, core body temperature sensors, skin temperature sensors, ultraviolet levels sensors, infrared sensors, ambient light sensors, gyroscope, accelerometer, EKG/ECG, magnetometer, sound level sensor (e.g., microphone), heart rate sensor, pulse oximetry sensor, hall effect sensor (e.g., magnetic field), respiration rate sensor, and galvanic skin sensor.

In some embodiments, sensors 114 may be configured to detect information transmitted by one or more beacons 110. For example, sensors 114 may be configured to receive and unpack a message transmitted by a beacon 110 to determine a relative position of wearable device 102.

Controller 116 may be configured to control operations of wearable device 102. For example, controller 116 may be configured to selectively deliver audio messages to the individual based on detected trigger conditions. Using a specific example, based on sensors 114 detecting the user falling, controller 116 may selectively identify a locally stored audio message that is relevant to the detected event, and may playback the audio message for the user.

Server system 104 may be configured to manage voice reminders for end users. As shown, server system 104 may include web client application server 118, application programming interface (API) server 120, and gateway server 122. Each of API server 120 and gateway server 122 may be comprised of one or more software modules. The one or more software modules are collections of code or instructions stored on a media (e.g., memory of server system 104) that represent a series of machine instructions (e.g., program code) that implements one or more algorithmic steps. Such machine instructions may be the actual computer code the processor of server system 104 interprets to implement the instructions or, alternatively, may be a higher level of coding of the instructions that are interpreted to obtain the actual computer code. The one or more software modules may also include one or more hardware components. One or more aspects of an example algorithm may be performed by the hardware components (e.g., circuitry) itself, rather than as a result of the instructions.

API server 120 may be configured to handle audio messages generated by an end user (e.g., user of client device 108) for upload to wearable device 102. For example, API server 120 may receive an audio message generated by client device 108. In some embodiments, the audio message may be received in base64 audio format. In such embodiments, API server 120 may be configured to decode the base64 audio message and may convert the decoded messages into a 16-bit or 16 KHz raw audio format (e.g., .wav format). In the converted format, API server 120 may upload the converted audio file to cloud storage 106. In some embodiments, cloud storage 106 may be representative of an Amazon Web Services® 53° bucket. In some embodiments, in addition to uploading the audio message in a converted format, API server 120 may be configured to upload the audio message in its original format, as a backup to the converted format in case the converted format becomes lost or corrupted.

In some embodiments, the uploading of the audio message to the converted format may generate a unique identifier and file path associated with the unique identifier. In some embodiments, the unique identifier and file path associated with the unique identifier can be saved in a separate storage location. For example, the unique identifier and file path associated with the unique identifier can be stored in a MYSQL database, accessible to gateway server 122 and/or client device 108 via a representational state transfer (REST) API. In some embodiments, API server 120 may provide the REST APIs to application 124 executing on client device 108 and/or application 112 executing on wearable device 102. In some embodiments, a REST API, customized for the application 124 on client device 108, may be dynamically generated by API server 120. In some embodiments, the REST API may be generated specifically for the use by a particular client device. In some embodiments, the REST API may be dynamically used by the client to access its own specialized data, such as specific messages and associated constraint data.

Gateway server 122 may be configured to communicate with wearable device 102 and/or cloud storage 106. Gateway server 122 may be configured to monitor cloud storage 106 and/or MYSQL database to determine when there is a new audio message or a modified audio message for each wearable device 102. Upon determining that a new audio message or a modified audio message is available, gateway server 122 may notify wearable device 102. Wearable device 102 may instruct gateway server 122 to download the new audio message or modified message from cloud storage 106. In some embodiments, gateway server 122 may format the retrieved audio message. For example, gateway server 122 may trim or reduce the audio message to a pre-set length (e.g., one minute or less). Gateway server 122 may then provide the audio message to wearable device 102.

Cloud storage 106 may be representative of one or more cloud service providers. Generally, cloud storage 106 may be representative of a cloud storage offering that is able to scale to the needs of server system 104.

Client device 108 may be in communication with server system 104 via network 105. Client device 108 may be operated by a user. For example, client device 108 may be a mobile device, a tablet, a desktop computer, or any computing system capable of recording or generating an audio message to be uploaded to server system 104 and/or provided to wearable device 102 for playback. Users may include, but are not limited to, individuals such as, for example, family members, clinicians, friends, and the like associated with a user of wearable device 102.

Client device 108 may include at least application 124. Application 124 may be representative of an application through which a user can record or generate an audio message for playback to a user of wearable device 102. In some embodiments, an audio message may be representative of a reminder. In some embodiments, an audio message may be representative of guidance or instructions for taking a physiological measurement (e.g., blood pressure, heart rate, glucose levels, and the like). In some embodiments, application 124 may be a standalone application associated with server system 104. In some embodiments, application 124 may be representative of a web-browser configured to communicate with server system 104. In some embodiments, client device 108 may communicate over network 105 to request a webpage, for example, from web client application server 118 of server system 104. For example, client device 108 may be configured to execute application 124 to generate or record an audio message. In some embodiments, client device 108 may define constraints associated with the audio message. Exemplary constraints may include, but are not limited to, an indication of the target recipient (e.g., user or patient identifier), a trigger condition associated with playback of the audio message, times to not play the video message (e.g., during sleeping hours), and the like. The content that is displayed to client device 108 may be transmitted from web client application server 118 to client device 108, and subsequently processed by application 124 for display through a graphical user interface (GUI) of client device 108.

In some embodiments, client device 108 may receive a notification when the generated audio message is played at wearable device 102. For example, for each audio message generated by client device 108, application 124 may include a status identifier associated therewith. The status identifier of a given audio message may be updated to reflect a playing of the audio message at wearable device 102. For example, in some embodiments, when wearable device 102 plays back the audio message, application 112 executing on wearable device 102 may send a notification to application 124 that the audio message was played. Application 124 may then update the status identifier associated with the played audio message.

Beacons 110 may be representative of a communication device configured to transmit or beacon a signal for receipt by one or more wearable devices 102. For example, beacons 110 may be representative of low power infrared beacons. Generally, beacons 110 may be configured to transmit a unique identifier representing the area of a venue in which they are affixed. Exemplary identifiers may include, but are not limited to, stove/kitchen, toilet/bathroom, bedroom, multi-purpose room, and the like. In some embodiments, beacons 110 may be self-installed devices that are fixed at a range of prescribed heights and operate on self-contained power or utility power.

Figure 2:
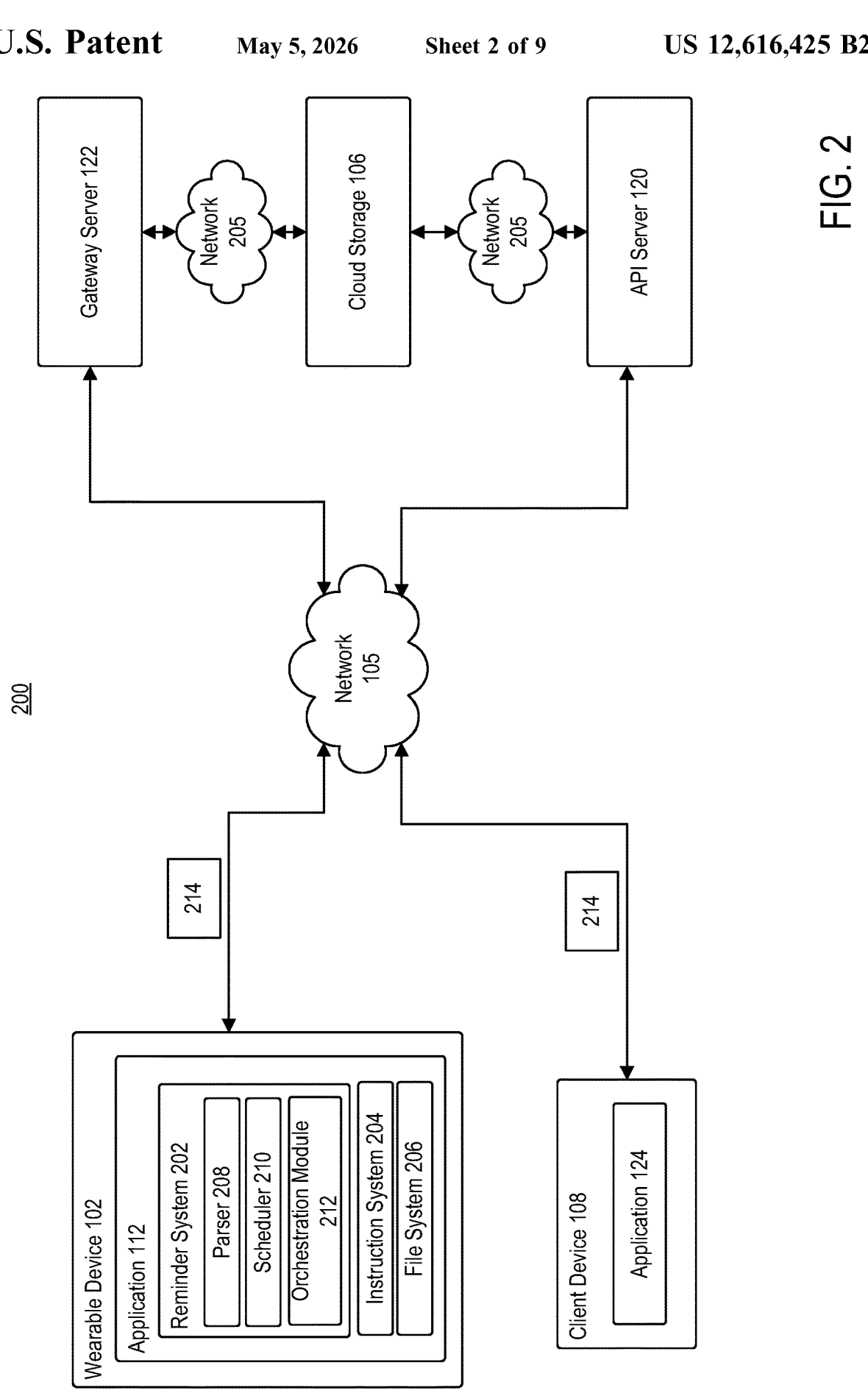
FIG. 2 is a block diagram illustrating a computing environment, according to example embodiments.

FIG. 2 is a block diagram illustrating a computing environment 200, according to example embodiments. Computing environment 200 may illustrate an exemplary process in which client device 108 generates a voice recording for a user of wearable device 102.

As shown, client device 108 may generate a new reminder audio message 214 using application 124. Application 124 may allow user of client device 108 to access functionality associated with server system 104. For example, via application 124, a user of client device 108 can record a message to be played to a user of wearable device 102 via wearable device 102. In some embodiments, the message can be a reminder message. In some embodiments, the message may be an instructions message. In some embodiments, user of client device 108 can set constraints or parameters associated with the recording using application 124. For example, client device 108 can dictate a trigger event for replaying the message. In some embodiments, the trigger event may be wearable device 102 detecting the user entered or approached a certain location. In some embodiments, the trigger event may be wearable device 102 detecting a certain user motion or activity. For example, the motion or activity may include, but is not limited to, eating, exercising, falling, brushing teeth, and the like. In some embodiments, the trigger event may be time based. For example, every night at 9:00 p.m., wearable device 102 may be instructed to play the message.

In some embodiments, application 112 of wearable device 102 may utilize a combination of sensors and algorithms to detect a location of the wearer (e.g., kitchen), an activity being performed by the wearer (e.g., cooking), and the like. In some embodiments, application 112 may utilize one or more kinematic algorithms trained to recognize a gesture (e.g., a fork lifting off a surface to the mouth, the repetition of which over certain times and certain locations to identify the event of eating). For example, the kinematic algorithms may be trained to track the position of the wrist in 3D space, its acceleration in x, y, and z axes (accelerometer), as well as the rotational vectors (gyroscope) to identify the movement of the hand from surface to mouth using an Inertial Measurement Unit (IMU) that may include a multi-axis accelerometer and a multi-axis gyroscope. In some embodiments, precision may be improved by using a multi-axis magnetometer and or an inclinometer or an orientation sensor.

In some embodiments, client device 108 may communicate with server system 104, via application 124, using one or more API calls. For example, when generating a new reminder audio message to be played to a user of wearable device 102, client device 108 may utilize a POST/v1/ schedule/audio API call. Such API call may generally be made by application 124 to create a new reminder audio message.

API server 120 may receive the API call from client device 108. For example, API server 120 may receive the new reminder audio message and any constraints associated with the new reminder audio message. Upon receiving the new reminder audio message, API server 120 may upload the audio file to cloud storage 106. In some embodiments, in addition to uploading the reminder audio message in a converted format, API server 120 may be configured to upload the reminder audio message in its original format, as a backup to the converted format in case the converted format becomes lost or corrupted.

In some embodiments, the uploading of the reminder audio message to the converted format may generate a unique identifier and file path associated with the unique identifier. In some embodiments, the unique identifier and file path associated with the unique identifier can be saved in a separate storage location. For example, the unique identifier and file path associated with the unique identifier can be stored in a MYSQL database, accessible to gateway server 122 and/or client device 108.

In some embodiments, gateway server 122 may monitor cloud storage 106. For example, gateway server 122 may monitor cloud storage 106 to determine when a new reminder audio message is uploaded. In some embodiments, gateway server 122 may monitor MYSQL database to determine when there is a new reminder audio message. In some embodiments, gateway server 122 may receive a notification that a new reminder audio message is available.

Upon determining that a new reminder audio message is available, gateway server 122 may notify wearable device 102 over network 105.

Wearable device 102 may instruct gateway server 122 to download new reminder audio message 214 from cloud storage 106. In some embodiments, gateway server 122 may format the retrieved reminder audio message. For example, gateway server 122 may trim or reduce the reminder audio message to a pre-set length (e.g., one minute or less). Gateway server 122 may then provide the reminder audio message to wearable device 102.

In some embodiments, gateway server 122, API server 120, and cloud storage 106 may communicate via a different network than network 105, i.e., network 205. By communicating via a separate network, client device 108 and/or wearable device 102 may not have direct access to cloud storage 106. Network 205 may be of any suitable type, including individual connections via the Internet, such as cellular or Wi-Fi networks. In some embodiments, network 205 may connect terminals, services, and mobile devices using direct connections, such as radio frequency identification (RFID), near-field communication (NFC), Bluetooth™, low-energy Bluetooth™ (BLE), Wi-Fi™, Zig-Bee™, ambient backscatter communication (ABC) protocols, USB, Long Range Wide area networks (LoRAWAN), WAN, or LAN. Because the information transmitted may be personal or confidential, security concerns may dictate one or more of these types of connection be encrypted or otherwise secured. In some embodiments, however, the information being transmitted may be less personal, and therefore, the network connections may be selected for convenience over security.

Network 205 may include any type of computer networking arrangement used to exchange data or information. For example, network 105 may be the Internet, a private data network, virtual private network using a public network and/or other suitable connection(s) that enables components in computing environment 100 to send and receive information between the components of environment 100.

As shown, application 112 of wearable device 102 may include reminder system 202, instruction system 204, and file system 206. Reminder system 202 may be configured to manage reminder audio messages. Instruction system 204 may be configured to manage instruction audio messages. For ease of illustration, the details of only reminder system 202 are discussed in FIGS. 2-5. The details of instruction system 204 may be found in more detail below, in conjunction with FIGS. 6-8.

Reminder system 202 may include parser 208, scheduler 210, and orchestration module 212. Each of parser 208, scheduler 210, and orchestration module 212 may be comprised of one or more software modules. The one or more software modules are collections of code or instructions stored on a media (e.g., memory of wearable device 102) that represent a series of machine instructions (e.g., program code) that implements one or more algorithmic steps. Such machine instructions may be the actual computer code the processor of wearable device 102 interprets to implement the instructions or, alternatively, may be a higher level of coding of the instructions that are interpreted to obtain the actual computer code. The one or more software modules may also include one or more hardware components. One or more aspects of an example algorithm may be performed by the hardware components (e.g., circuitry) itself, rather than as a result of the instructions.

Parser 208 may be configured to parse reminder audio message 214. For example, as previously discussed, gateway server 122 may provide the reminder audio message to wearable device 102 in the form of a JSON file. Parser 208 may be configured to parse the JSON file to obtain details regarding playback of the reminder audio message. For example, parser 208 may parse JSON file to identify the constraints or parameters for playback, as defined by client device 108. Parser 208 may be configured to store the reminder audio message and/or associated constraints or parameters in file system 206. File system 206 may be configured to organize the audio files associated with wearable device 102.

Scheduler 210 may be configured to schedule reminder audio messages for playback. For example, scheduler 210 may monitor or check file system 206 to determine when to playback a reminder audio message. In some embodiments, scheduler 210 may be configured to playback a reminder audio message in accordance with time constraints set by user of client device 108. For example, if client device 108 set a constraint that the reminder audio message should be played back at 9:00 p.m., scheduler 210 may schedule the reminder audio message to be played at 9:00 p.m.

Orchestration module 212 may be configured to monitor trigger events for determine when to play a reminder audio message. In some embodiments, orchestration module 212 may be configured to monitor communications from beacons 110 to determine if a location-based trigger occurs. In some embodiments, orchestration module 212 may be configured to monitor sensor data collected by sensors 114 to determine when whether an activity trigger has occurred. Based on the detected trigger events, orchestration module 212 may cause an appropriate or relevant reminder audio message to be played back to the user of wearable device 102.

In some embodiments, orchestration module 212 may be configured to control a light of wearable device 102. For example, in some embodiments, wearable device 102 may include an LED. Prior to a reminder audio message being played back, orchestration module 212 may cause LED to illuminate, to notify the user of wearable device 102 that a reminder audio message is about to be played. In some embodiments, rather than illuminate an LED or other light associated with wearable device 102, orchestration module 212 may cause wearable device 102 to provide the user with haptic feedback to notify the user that a reminder audio message is about to be played.

Figure 3:
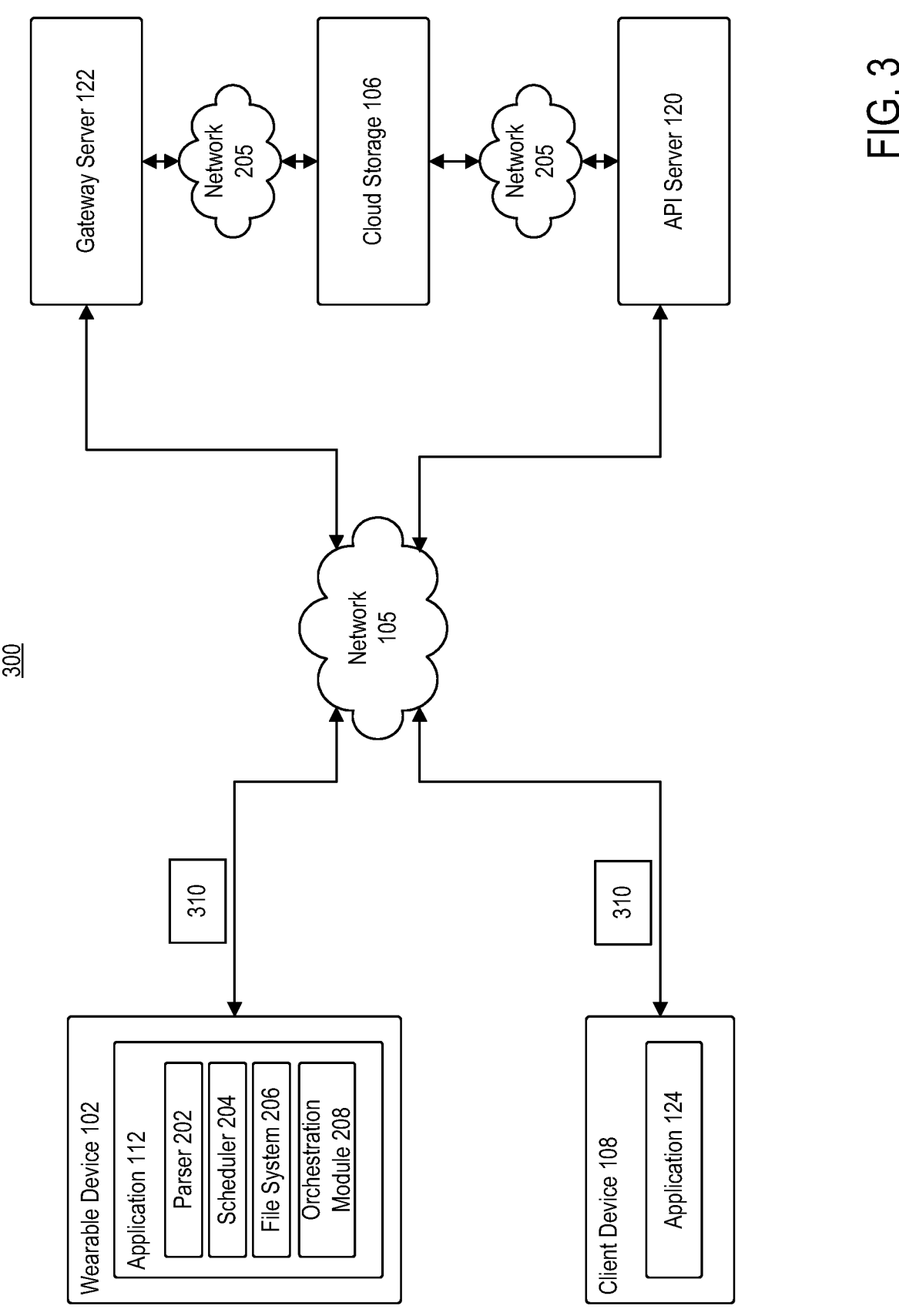
FIG. 3 is a block diagram illustrating a computing environment, according to example embodiments.

FIG. 3 is a block diagram illustrating a computing environment 300, according to example embodiments. Computing environment 200 may illustrate an exemplary process in which client device 108 generates an update to an existing voice recording for a user of wearable device 102.

As shown, client device 108 may generate a modification 310 to an existing recording that has been uploaded to cloud storage 106 via application 124. In some embodiments, modification 310 may be to the audio recording itself. For example, a user of client device 108 may wish to modify the existing audio recording with a new or modified message. In some embodiments, modification 310 may be to the parameters or constraints associated with the audio recording. For example, a user of client device 108 may wish to modify when an audio recording is played or the trigger event(s) associated with the audio recording. Using a specific example, a user of client device 108 may wish to modify the playback time for the reminder audio message from 9:00 p.m. to 8:00 p.m.

In some embodiments, client device 108 may communicate with server system 104, via application 124, using one or more API calls. For example, when a user generates modification 310, client device 108 may utilize a PUT/v1/schedule/audio/{careVoiceId} API call. Such API call may generally be made by application 124 to update or modify an existing reminder audio message.

API server 120 may receive the API call from client device 108. For example, API server 120 may receive modification 310. Upon receiving modification, API server 120 may adjust the existing reminder audio message corresponding to modification 310. In some embodiments, updating the existing reminder audio message may include writing over an existing reminder audio message with the new reminder audio message. In some embodiments, updating constraints or parameters associated with the existing reminder audio message may include API server 120 updating metadata associated with the existing reminder audio message.

In some embodiments, gateway server 122 may monitor cloud storage 106 for updates. For example, gateway server 122 may monitor cloud storage 106 to determine when a modification to an existing reminder audio message is uploaded. In some embodiments, gateway server 122 may monitor MYSQL database to determine when there is a modification. In some embodiments, gateway server 122 may receive a notification that there has been a modification to an existing reminder audio message. Upon determining that modification 310, gateway server 122 may notify wearable device 102 over network 105.

Wearable device 102 may instruct gateway server 122 to download modification 310 from cloud storage 106. Gateway server 122 may provide modification 310 to wearable device 102. In some embodiments, parser 208 of wearable device 102 may parse modification 310 to determine how to adjust or change a local version of the existing reminder audio message. In some embodiments, adjusting or changing the local version of the existing reminder audio message may include parser 208 overwriting the existing reminder audio message with modification 310. In some embodiments, adjusting or changing the local version of the existing reminder audio message may include parser 208 changing or modifying constraints or parameters of the existing reminder audio message based on modification 310.

Figure 4B:
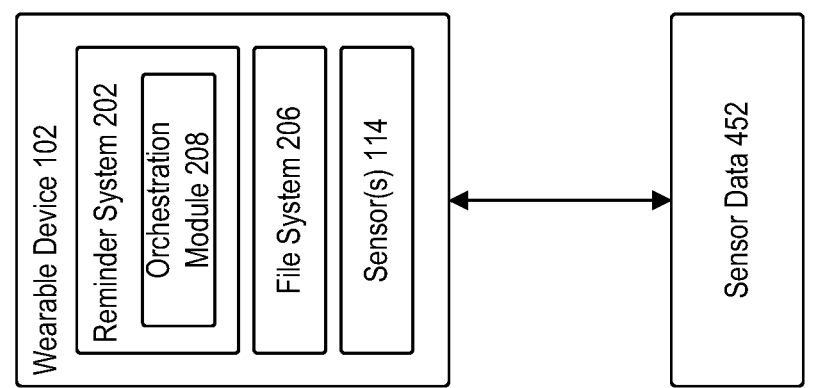
FIG. 4B is a block diagram illustrating a computing environment, according to example embodiments.
Figure 4A:
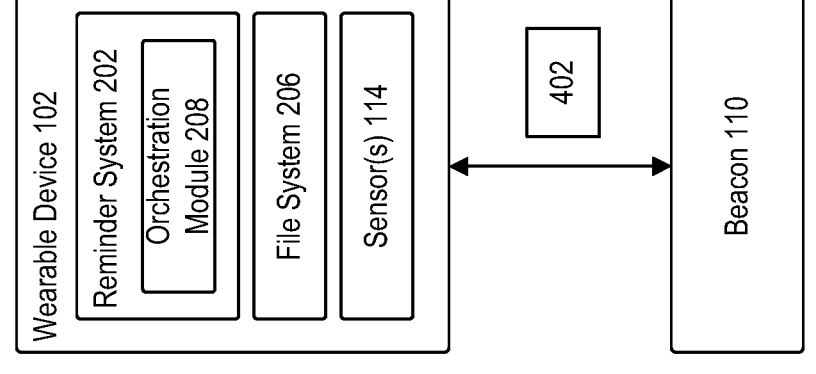
FIG. 4A is a block diagram illustrating a computing environment, according to example embodiments.

FIG. 4A is a block diagram illustrating a computing environment 400, according to example embodiments. Computing environment 400 may illustrate an exemplary process in which wearable device 102 identifies a location-based trigger for playback of a reminder audio message.

As shown, wearable device 102 may receive a communication 402 from beacon 110. Communication 402 may include information associated with the relative positioning of wearable device 102. For example, when a wearable device 102 comes within range of beacon 110, wearable device 102 may receive communication 402 from beacon 110. Communication 402 includes information regarding the location of wearable device 102. For example, communication 402 may specify that beacon 110 corresponds to "kitchen" and that the user is approaching the kitchen, since wearable device 102 is able to receive communications from beacon 110 (i.e., is within range).

In some embodiments, orchestration module 212 may be configured to parse communication 402 to determine an appropriate reminder audio message (if any) to playback to the user. For example, based on information contained in communication 402, such as location information, orchestration module 212 may search file system 206 for a corresponding reminder audio message. Orchestration module 212 may then cause the corresponding reminder audio message to be played back to the user.

FIG. 4B is a block diagram illustrating a computing environment 450, according to example embodiments. Computing environment 450 may illustrate an exemplary process in which wearable device 102 identifies an activity-based trigger for playback of a reminder audio message.

As shown, wearable device 102 may receive a sensor data 452. For example, sensors 114 may measure various attributes associated with the user. Exemplary sensor data 452 may include, but is not limited to, heart rate, blood pressure, speed, velocity, hydration levels, elevation, and the like. Orchestration module 212 may be configured to parse sensor data 452 to determine an appropriate reminder audio message (if any) to playback to the user. For example, based on information contained in sensor data 452, such as an indication of a user falling, orchestration module 212 may search file system 206 for a corresponding reminder audio message. Orchestration module 212 may then cause the corresponding reminder audio message to be played back to the user.

FIG. 5 is a flow diagram illustrating a method 500 of playing back a reminder audio message to a user of wearable device 102, according to example embodiments. Method 500 may begin at step 502.

At step 502, client device 108 may generate a new audio recording to be played back via wearable device 102. In some embodiments, client device 108 may generate the new audio recording using application 124. For example, via application 124, a user of client device 108 can record a reminder audio message to be played to a user of wearable device 102 via wearable device 102. In some embodiments, user of client device 108 can set constraints or parameters associated with the recording using application 124. For example, client device 108 can dictate a trigger event for replaying the message. In some embodiments, the trigger event may be wearable device 102 detecting the user entered or approached a certain location. In some embodiments, the trigger event may be wearable device 102 detecting a certain user motion or activity. In some embodiments, the trigger event may be time based.

At 504, client device 108 may upload the new reminder audio message to server system 104. For example, via application 124, client device 108 may upload the new reminder audio message to server system 104. In some embodiments, client device 108 may communicate with server system 104 using one or more API calls. For example, client device 108 may utilize a POST/v1/schedule/audio API call.

At step 506, API server 120 of server system 104 may upload the reminder audio message to cloud storage 106. For example, API server 120 may receive an API call from client device 108. The API call may include the new reminder audio message and any constraints or parameters associated with the new reminder audio message. In some embodiments, the reminder audio message may be received in base64 audio format. In such embodiments, API server 120 may decode the base64 reminder audio message and may convert the decoded messages into a 16-bit or 16 KHz raw audio format (e.g., .wav format). In the converted format, API server 120 may upload the converted audio file to cloud storage 106. In some embodiments, in addition to uploading the reminder audio message in a converted format, API server 120 may upload the reminder audio message in its original format, as a backup to the converted format in case the converted format becomes lost or corrupted.

At step 508, API server 120 may save a storage location of reminder audio message in cloud storage 106 in a database. In some embodiments, the uploading of the reminder audio message to the converted format may generate a unique identifier and file path associated with the unique identifier. In some embodiments, the unique identifier and file path associated with the unique identifier can be saved in a separate storage location.

At step 510, gateway server 122 may detect the new reminder audio message in cloud storage 106. For example, in some embodiments, gateway server 122 may monitor cloud storage 106 to determine when a new reminder audio message is uploaded. In some embodiments, gateway server 122 may monitor MYSQL database to determine when there is a new reminder audio message. In some embodiments, gateway server 122 may receive a notification that a new reminder audio message is available.

At step 512, gateway server 122 may notify wearable device 102 that a new reminder audio message is available for download. At step 514, wearable device 102 may receive notification of the new reminder audio message from gateway server 122. At step 516, wearable device 102 may instruct server system 104 to provide the new reminder audio message. For example, wearable device 102 may utilize one or more REST API calls to gateway server 122 to prompt gateway server 122 to provide wearable device 102 with the new reminder audio message.

At step 518, gateway server 122 may receive the download instructions from wearable device 102. At step 520, gateway server 122 may download the new reminder audio message from cloud storage 106. For example, in order to provide wearable device 102 with the new reminder audio message, gateway server 122 may first retrieve the new reminder audio message from cloud storage 106. Such retrieval may be necessary because, in some embodiments, wearable device 102 may not have direct access to cloud storage 106. In some embodiments, gateway server 122 may format the retrieved reminder audio message. For example, gateway server 122 may trim or reduce the reminder audio message to a pre-set length (e.g., one minute or less). Gateway server 122 may then provide the reminder audio message to wearable device 102.

At step 522, gateway server 122 may provide the new reminder audio message to wearable device 102. At step 524, wearable device 102 may receive the new reminder audio message from server system 104.

At step 526, wearable device 102 may save the new reminder audio message in local storage. For example, wearable device 102 may parse the reminder audio message to obtain details regarding playback of the reminder audio message. For example, parser 208 of wearable device 102 may parse the file provided by gateway server 122 to identify constraints or parameters for playback, as defined by client device 108. Wearable device 102 may store the reminder audio message and/or associated constraints or parameters in file system 206.

At step 528, wearable device 102 may detect a trigger event. In some embodiments, the trigger event may be wearable device 102 detecting the user entered or approached a certain location. In some embodiments, the trigger event may be wearable device 102 detecting a certain user motion or activity. For example, the motion or activity may include, but is not limited to, exercising, falling, brushing teeth, and the like. In some embodiments, the trigger event may be time based. For example, every night at 9:00 p.m., wearable device 102 may be instructed to play the message.

At step 530, wearable device 102 may play the reminder audio message corresponding to the trigger event. For example, upon detecting the trigger event, orchestration module 212 of wearable device 102 may search file system 206 to identify a relevant reminder audio message. In some embodiments, the relevant reminder audio message may be the new reminder audio message. Responsive to identifying the relevant reminder audio message, orchestration module 212 may cause wearable device 102 to playback the new reminder audio message.

FIG. 6 is a block diagram illustrating a computing environment 600, according to example embodiments. Computing environment 600 may illustrate an exemplary process in which client device 108 generates an instruction audio message for a user of wearable device 102.

As discussed above, client device 108 can record a message to be played to a user of wearable device 102 via wearable device 102. In some embodiments, the message may be an instructions message. In some embodiments, user of client device 108 can set constraints or parameters associated with the instructions message using application 124. For example, client device 108 can dictate a trigger event (e.g., a time and/or date) for replaying the message.

In some embodiments, client device 108 may communicate with server system 104, via application 124, using one or more API calls. For example, when generating a new instruction audio message to be played to a user of wearable device 102, client device 108 may utilize a POST/v1/schedule/audio API call. Such API call may generally be made by application 124 to create a new instruction audio message.

API server 120 may receive the API call from client device 108. For example, API server 120 may receive the new instruction audio message and any constraints associated with the new instruction audio message. Upon receiving the new instruction audio message, API server 120 may upload the audio file to cloud storage 106. In some embodiments, in addition to uploading the instruction audio message in a converted format, API server 120 may be configured to upload the instruction audio message in its original format, as a backup to the converted format in case the converted format becomes lost or corrupted.

In some embodiments, the uploading of the instruction audio message to the converted format may generate a unique identifier and file path associated with the unique identifier. In some embodiments, the unique identifier and file path associated with the unique identifier can be saved in a separate storage location. For example, the unique identifier and file path associated with the unique identifier can be stored in a MYSQL database, accessible to gateway server 122 and/or client device 108.

In some embodiments, gateway server 122 may monitor cloud storage 106. For example, gateway server 122 may monitor cloud storage 106 to determine when a new instruction audio message is uploaded. In some embodiments, gateway server 122 may monitor MYSQL database to determine when there is a new instruction audio message. In some embodiments, gateway server 122 may receive a notification that a new instruction audio message is available. Upon determining that a new instruction audio message is available, gateway server 122 may notify wearable device 102 over network 105.

Wearable device 102 may instruct gateway server 122 to download new instruction audio message 614 from cloud storage 106. In some embodiments, gateway server 122 may format the retrieved instruction audio message. For example, gateway server 122 may trim or reduce the instruction audio message to a pre-set length (e.g., one minute or less). Gateway server 122 may then provide the instruction audio message to wearable device 102.

In some embodiments, gateway server 122, API server 120, and cloud storage 106 may communicate via a different network than network 105, i.e., network 205. By communicating via a separate network, client device 108 and/or wearable device 102 may not have direct access to cloud storage 106. Network 205 may be of any suitable type, including individual connections via the Internet, such as cellular or Wi-Fi networks. In some embodiments, network 205 may connect terminals, services, and mobile devices using direct connections, such as radio frequency identification (RFID), near-field communication (NFC), Bluetooth™, low-energy Bluetooth™ (BLE), Wi-Fi™, ZigBee™, ambient backscatter communication (ABC) protocols, USB, Long Range Wide area networks (LoRAWAN), WAN, or LAN. Because the information transmitted may be personal or confidential, security concerns may dictate one or more of these types of connection be encrypted or otherwise secured. In some embodiments, however, the information being transmitted may be less personal, and therefore, the network connections may be selected for convenience over security.

Network 205 may include any type of computer networking arrangement used to exchange data or information. For example, network 105 may be the Internet, a private data network, virtual private network using a public network and/or other suitable connection(s) that enables components in computing environment 100 to send and receive information between the components of environment 100.

As shown, application 112 of wearable device 102 may include reminder system 202, instruction system 204, and file system 206. The details of reminder system 202 has been discussed above in conjunction with FIGS. 2-5.

Instruction system 204 may include parser 608, scheduler 610, and orchestration module 612. Each of parser 608, scheduler 610, and orchestration module 612 may be comprised of one or more software modules. The one or more software modules are collections of code or instructions stored on a media (e.g., memory of wearable device 102) that represent a series of machine instructions (e.g., program code) that implements one or more algorithmic steps. Such machine instructions may be the actual computer code the processor of wearable device 102 interprets to implement the instructions or, alternatively, may be a higher level of coding of the instructions that are interpreted to obtain the actual computer code. The one or more software modules may also include one or more hardware components. One or more aspects of an example algorithm may be performed by the hardware components (e.g., circuitry) itself, rather than as a result of the instructions.

Parser 608 may be configured to parse instruction audio message 614. For example, as previously discussed, gateway server 122 may provide the instruction audio message to wearable device 102 in the form of a JSON file. Parser 608 may be configured to parse the JSON file to obtain details regarding playback of the audio message. For example, parser 608 may parse JSON file to identify the constraints or parameters for playback, as defined by client device 108. Parser 608 may be configured to store the audio message and/or associated constraints or parameters in file system 206. File system 206 may be configured to organize the audio files associated with wearable device 102.

Scheduler 610 may be configured to schedule audio messages for playback. For example, scheduler 610 may monitor or check file system 206 to determine when to playback an audio message. In some embodiments, scheduler 610 may be configured to playback an audio message in accordance with time constraints set by user of client device

108. For example, if client device 108 set a constraint that the audio message should be played back at 9:00 p.m., scheduler 610 may schedule the audio message to be played at 9:00 p.m.

Orchestration module 612 may be configured to manage the playback of the instruction audio message. For example, in some embodiments, a patient or creator of the instruction audio message can define one or more "quiet times." During quiet times, orchestration module 612 may defer reminders that are scheduled to fall within that time period.

In some embodiments, orchestration module 612 may be configured to take into account a patient's current context to adaptively decide to play or not play a reminder, or to play or not play a message based on the occurrence or non-occurrence of a particular event (e.g., prompt glucose measurement thirty minutes after eating was last detected).

In some embodiments, orchestration module 612 may further be configured connect to a measurement device when instruction audio message for taking a measurement is played. In some embodiments, orchestration module 612 may be configured to recognize, via Bluetooth or other local area communication protocols, measuring apparatus 615. In some embodiments, orchestration module 612 may be configured to automatically pair with measuring apparatus 615, to pair with measuring apparatus 615 using pre-configured identifiers, codes or passwords, and receive data from measuring apparatus 615 without further user intervention. Orchestration module 612 may then send the measurements to server system 104 for storage thereon. Server system 104 may then organize and display this measurement data to the user through a web and mobile application. Server system 104 can raise alerts to individuals based on their authorization and scope of interest and on certain levels or ranges of measurements.

In some embodiments, once the data is received from measuring apparatus 615, orchestration module 612 may be configured to read back the measurements to the patient. In some embodiments, orchestration module 612 may utilize one or more pre-recorded audio files, which may be dynamically constructed from various segments of pre-recorded audio, to generate the playback message.

In some embodiments, orchestration module 612 may be configured to control a light of wearable device 102. For example, in some embodiments, wearable device 102 may include an LED. Prior to an instruction audio message being played back, orchestration module 612 may cause LED to illuminate, to notify the user of wearable device 102 that an instruction audio message is about to be played. In some embodiments, rather than illuminate an LED or other light associated with wearable device 102, orchestration module 612 may cause wearable device 102 to provide the user with haptic feedback to notify the user that an instruction audio message is about to be played.

FIG. 7A is a block diagram illustrating a computing environment 700, according to example embodiments. Computing environment 700 may illustrate an exemplary process in which wearable device 102 identifies a context-based trigger for playback of an audio message.

As shown, wearable device 102 may receive a sensor data 706. For example, sensors 114 may measure various attributes associated with the user. Exemplary sensor data 706 may include, but is not limited to, heart rate, blood pressure, speed, velocity, hydration levels, elevation, and the like. Orchestration module 612 may be configured to parse sensor data 706 to determine an appropriate instruction message (if any) to playback to the user. For example, based on information contained in sensor data 706, orchestration module

612 may determine that the user should take a physiological measurement and may search file system 206 for a corresponding instruction audio message. Orchestration module 612 may then cause the corresponding audio message to be played back to the user.

FIG. 7B is a block diagram illustrating a computing environment 750, according to example embodiments. Computing environment 750 may illustrate an exemplary process in which wearable device 102 plays back an instruction audio message and connects to an appropriate measuring apparatus 615.

As shown, wearable device 102 may select an instruction audio message to be played back to the user based on sensor data 706. For example, orchestration module 612 may determine that the patient should take a glucose reading thirty minutes after they ate. Based on the selected instruction audio message, orchestration module 612 may instruct communication interface 702 to pair or connect with an appropriate measuring apparatus 615. Continuing with the above example, orchestration module 612 may instruct communication interface to pair or connect with a glucose measuring apparatus. Once connected, wearable device 102 may playback instructions to the patient regarding how to take a measurement using measuring apparatus 615.

Figure 8:
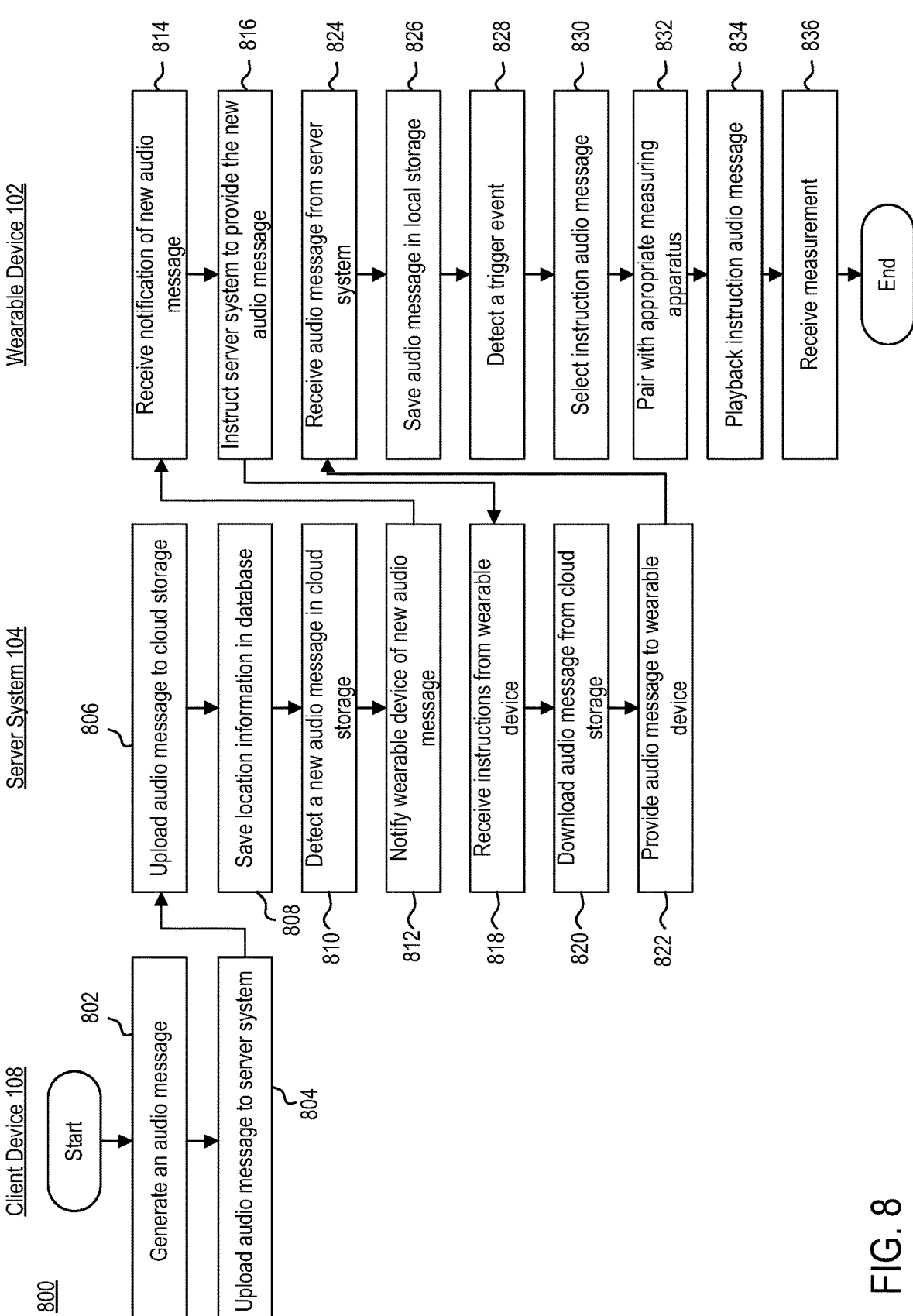
FIG. 8 is a flow diagram illustrating a method of playing back an instruction audio message to a user of wearable device, according to example embodiments.

FIG. 8 is a flow diagram illustrating a method 800 of playing back an instruction audio message to a user of wearable device 102, according to example embodiments. Method 800 may begin at step 802.

At step 802, client device 108 may generate a new audio recording to be played back via wearable device 102. In some embodiments, client device 108 may generate the new audio recording using application 124. For example, via application 124, a user of client device 108 can record an instruction audio message to be played to a user of wearable device 102 via wearable device 102. In some embodiments, user of client device 108 can set constraints or parameters associated with the recording using application 124. For example, client device 108 can dictate a trigger event for replaying the message. In some embodiments, the trigger event may be wearable device 102 detecting the user entered or approached a certain location. In some embodiments, the trigger event may be wearable device 102 detecting a certain user motion or activity. In some embodiments, the trigger event may be time based.

At 804, client device 108 may upload the new instruction audio message to server system 104. For example, via application 124, client device 108 may upload the new instruction audio message to server system 104. In some embodiments, client device 108 may communicate with server system 104 using one or more API calls. For example, client device 108 may utilize a POST/v1/schedule/audio API call.

At step 806, API server 120 of server system 104 may upload the instruction audio message to cloud storage 106. For example, API server 120 may receive an API call from client device 108. The API call may include the new instruction audio message and any constraints or parameters associated with the new instruction audio message. In some embodiments, the instruction audio message may be received in base64 audio format. In such embodiments, API server 120 may decode the base64 instruction audio message and may convert the decoded messages into a 16-bit or 16 KHz raw audio format (e.g., .wav format). In the converted format, API server 120 may upload the converted audio file to cloud storage 106. In some embodiments, in addition to uploading the instruction audio message in a converted format, API server 120 may upload the instruction audio message in its original format, as a backup to the converted format in case the converted format becomes lost or corrupted.

At step 808, API server 120 may save a storage location of instruction audio message in cloud storage 106 in a database. In some embodiments, the uploading of the instruction audio message to the converted format may generate a unique identifier and file path associated with the unique identifier. In some embodiments, the unique identifier and file path associated with the unique identifier can be saved in a separate storage location.

At step 810, gateway server 122 may detect the new instruction audio message in cloud storage 106. For example, in some embodiments, gateway server 122 may monitor cloud storage 106 to determine when a new instruction audio message is uploaded. In some embodiments, gateway server 122 may monitor MYSQL database to determine when there is a new instruction audio message. In some embodiments, gateway server 122 may receive a notification that a new instruction audio message is available.

At step 812, gateway server 122 may notify wearable device 102 that a new instruction audio message is available for download. At step 814, wearable device 102 may receive notification of the new instruction audio message from gateway server 122. At step 816, wearable device 102 may instruct server system 104 to provide the new instruction audio message. For example, wearable device 102 may utilize one or more REST API calls to gateway server 122 to prompt gateway server 122 to provide wearable device 102 with the new instruction audio message.

At step 818, gateway server 122 may receive the download instructions from wearable device 102. At step 820, gateway server 122 may download the new instruction audio message from cloud storage 106. For example, in order to provide wearable device 102 with the new instruction audio message, gateway server 122 may first retrieve the new instruction audio message from cloud storage 106. Such retrieval may be necessary because, in some embodiments, wearable device 102 may not have direct access to cloud storage 106. In some embodiments, gateway server 122 may format the retrieved instruction audio message. For example, gateway server 122 may trim or reduce the instruction audio message to a pre-set length (e.g., one minute or less). Gateway server 122 may then provide the instruction audio message to wearable device 102.

At step 822, gateway server 122 may provide the new instruction audio message to wearable device 102. At step 824, wearable device 102 may receive the new instruction audio message from server system 104.

At step 826, wearable device 102 may save the new instruction audio message in local storage. For example, wearable device 102 may parse the instruction audio message to obtain details regarding playback of the instruction audio message. For example, parser 208 of wearable device 102 may parse the file provided by gateway server 122 to identify constraints or parameters for playback, as defined by client device 108. Wearable device 102 may store the instruction audio message and/or associated constraints or parameters in file system 206.

At step 828, wearable device 102 may detect a trigger event. In some embodiments, the trigger event may be wearable device 102 detecting the user entered or approached a certain location. In some embodiments, the trigger event may be wearable device 102 detecting a certain user motion or activity. For example, the motion or activity may include, but is not limited to, exercising, falling, brushing teeth, and the like. In some embodiments, the trigger event may be time based. For example, every night at 9:00 p.m., wearable device 102 may be instructed to play the message. In some embodiments, the trigger event may be manually actuated by the patient. For example, the patient may request a blood pressure measurement using wearable device 102. For example, in some embodiments, a user can press a button on wearable device 102. Pressing the button on wearable device 102 may prompt wearable device 102 to read out a menu of options. The menu of options may include various physiological measurements the user can take. The user may select any of the options provided in the menu of options.

At step 830, wearable device 102 may select an appropriate audio message based on the trigger event. In some embodiments, wearable device 102 may select an instruction audio message to be played back to the user based on sensor data. For example, orchestration module 612 may determine that the patient should take a glucose reading thirty minutes after they ate.

At step 832, wearable device 102 may pair or connect with an appropriate measuring apparatus based on the selected audio message. In some embodiments, orchestration module 612 may instruct communication interface 702 to pair or connect with an appropriate measuring apparatus 615. Continuing with the above example, orchestration module 612 may instruct communication interface to pair or connect with a glucose measuring apparatus. Once connected, wearable device 102 may playback instructions to the patient regarding how to take a measurement using measuring apparatus 615.

At step 834, wearable device 102 may play the instruction audio message corresponding to the trigger event. For example, once paired, orchestration module 612 may playback the instruction audio message. The instruction audio message may instruct the user on the steps required for obtaining a measurement using the connected measurement apparatus.

At step 836, wearable device 102 may receive measurement data from the connected measurement apparatus.

Figures 9A, 9B:
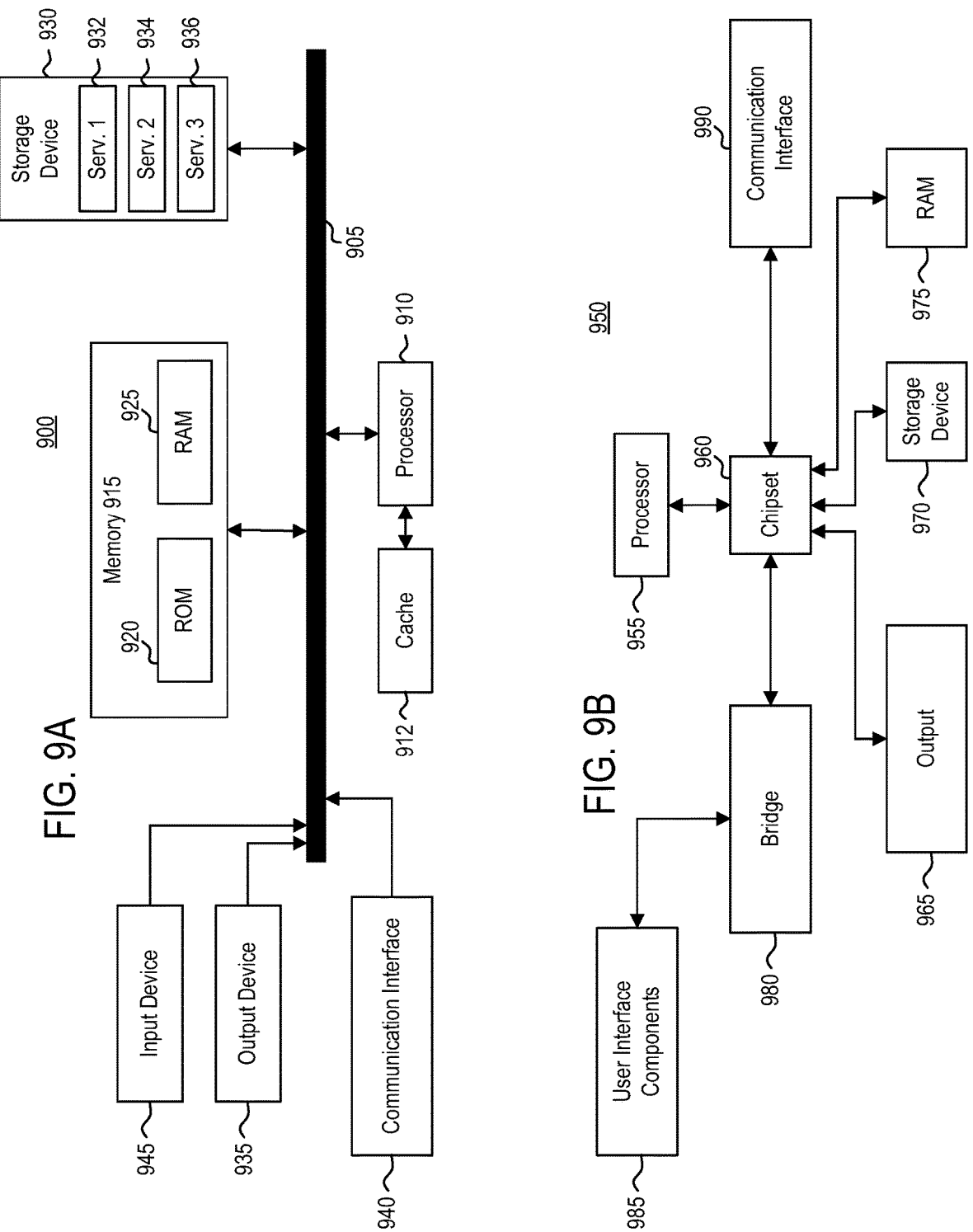
FIG. 9A is a block diagram illustrating a computing device, according to example embodiments.
FIG. 9B is a block diagram illustrating a computing device, according to example embodiments.

FIG. 9A illustrates an architecture of computing system 900, according to example embodiments. System 900 may be representative of at least a portion of server system 104. One or more components of system 900 may be in electrical communication with each other using a bus 905. System 900 may include a processing unit (CPU or processor) 910 and a system bus 905 that couples various system components including the system memory 915, such as read only memory (ROM) 920 and random access memory (RAM) 925, to processor 910. System 900 may include a cache of high-speed memory connected directly with, in close proximity to, or integrated as part of processor 910. System 900 may copy data from memory 915 and/or storage device 930 to cache 912 for quick access by processor 910. In this way, cache 912 may provide a performance boost that avoids processor 910 delays while waiting for data. These and other modules may control or be configured to control processor 910 to perform various actions. Other system memory 915 may be available for use as well. Memory 915 may include multiple different types of memory with different performance characteristics. Processor 910 may include any general purpose processor and a hardware module or software module, such as service 1 932, service 2 934, and service 3 936 stored in storage device 930, configured to control processor 910 as well as a special-purpose processor where software instructions are incorporated into the actual processor design. Processor 910 may essentially be a completely self-contained computing system, containing multiple cores or processors, a bus, memory controller, cache, etc. A multi-core processor may be symmetric or asymmetric.

To enable user interaction with the computing system 900, an input device 945 may represent any number of input mechanisms, such as a microphone for speech, a touch-sensitive screen for gesture or graphical input, keyboard, mouse, motion input, speech and so forth. An output device 935 (e.g., display) may also be one or more of a number of output mechanisms known to those of skill in the art. In some instances, multimodal systems may enable a user to provide multiple types of input to communicate with computing system 900. Communications interface 940 may generally govern and manage the user input and system output. There is no restriction on operating on any particular hardware arrangement and therefore the basic features here may easily be substituted for improved hardware or firmware arrangements as they are developed.

Storage device 930 may be a non-volatile memory and may be a hard disk or other types of computer readable media which may store data that are accessible by a computer, such as magnetic cassettes, flash memory cards, solid state memory devices, digital versatile disks, cartridges, random access memories (RAMs) 925, read only memory (ROM) 920, and hybrids thereof.

Storage device 930 may include services 932, 934, and 936 for controlling the processor 910. Other hardware or software modules are contemplated. Storage device 930 may be connected to system bus 905. In one aspect, a hardware module that performs a particular function may include the software component stored in a computer-readable medium in connection with the necessary hardware components, such as processor 910, bus 905, output device 935, and so forth, to carry out the function.

FIG. 9B illustrates a computer system 950 having a chipset architecture that may represent at least a portion of server system 104. Computer system 950 may be an example of computer hardware, software, and firmware that may be used to implement the disclosed technology. System 950 may include a processor 955, representative of any number of physically and/or logically distinct resources capable of executing software, firmware, and hardware configured to perform identified computations. Processor 955 may communicate with a chipset 960 that may control input to and output from processor 955. In this example, chipset 960 outputs information to output 965, such as a display, and may read and write information to storage device 970, which may include magnetic media, and solid-state media, for example. Chipset 960 may also read data from and write data to RAM 975. A bridge 980 for interfacing with a variety of user interface components 985 may be provided for interfacing with chipset 960. Such user interface components 985 may include a keyboard, a microphone, touch detection and processing circuitry, a pointing device, such as a mouse, and so on. In general, inputs to system 950 may come from any of a variety of sources, machine generated and/or human generated.

Chipset 960 may also interface with one or more communication interfaces 990 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 955 analyzing data stored in storage device 970 or RAM 975. Further, the machine may receive inputs from a user through user interface components 985 and execute appropriate functions, such as browsing functions by interpreting these inputs using processor 955.

It may be appreciated that example systems 900 and 950 may have more than one processor 910 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

What is claimed is:

1. A method, comprising:

detecting, by a wearable device, a trigger event, wherein the trigger event indicates a type of measurement to take, wherein detecting the trigger event comprises:

determining a location of a user wearing the wearable device based on beacon signals received from beacons in communication range of the wearable device, and inferring a perceived state of the user based on the determined location of the user and motions detected by one or more sensors of the wearable device;

based on the trigger event, selecting, by the wearable device, an instruction audio message corresponding to the type of measurement to be taken, the instruction audio message comprising instructions for how to conduct the type of measurement;

connecting, by the wearable device, to an appropriate measuring apparatus based on the type of measurement to be taken and the instruction audio message by identifying the appropriate measuring apparatus from among a plurality of possible measuring apparatuses and automatically pairing with the measuring apparatus using pre-configured identifiers, codes, or passwords to establish the connection without further user intervention;

playing, by the wearable device, the instruction audio message to a patient of the wearable device; and receiving, by the wearable device, measurements from the appropriate measuring apparatus.

2. The method of claim 1, further comprising:

causing, by the wearable device, a visual or physical notification that indicates the instruction audio message is to be played.

3. The method of claim 1, wherein detecting, by the wearable device, the trigger event, comprises:

receiving a prompt from the patient associated with the wearable device to record the type of measurement.

4. The method of claim 1, wherein detecting, by the wearable device, the trigger event, comprises:

analyzing, via one or more sensors of the wearable device, patient activity data to detect the trigger event.

5. The method of claim 1, wherein playing, by the wearable device, the instruction audio message to the patient of the wearable device comprises:

constructing the instruction audio message from a plurality of segments of pre-recorded audio.

6. A non-transitory computer readable medium comprising one or more sequences of instructions, which, when executed by one or more processors, causes a wearable device to perform operations comprising:

detecting, by the wearable device, a trigger event, wherein the trigger event indicates a type of measurement to take, wherein detecting the trigger event comprises:

determining a location of a user wearing the wearable device based on beacon signals received from beacons in communication range of the wearable device, and inferring a perceived state of the user based on the determined location of the user and motions detected by one or more sensors of the wearable device;

based on the trigger event, selecting, by the wearable device, an instruction audio message corresponding to the type of measurement to be taken, the instruction audio message comprising instructions for how to conduct the type of measurement;

connecting, by the wearable device, to an appropriate measuring apparatus based on the type of measurement to be taken and the instruction audio message by identifying the appropriate measuring apparatus from among a plurality of possible measuring apparatuses and automatically pairing with the measuring apparatus using pre-configured identifiers, codes, or passwords to establish the connection without further user intervention;

playing, by the wearable device, the instruction audio message to a patient of the wearable device; and receiving, by the wearable device, measurements from the appropriate measuring apparatus.

7. The non-transitory computer readable medium of claim 6, further comprising:

causing, by the wearable device, a visual or physical notification that indicates the instruction audio message is to be played.

8. The non-transitory computer readable medium of claim 6, wherein detecting, by the wearable device, the trigger event comprises:

receiving a prompt from the patient associated with the wearable device to record the type of measurement.

9. The non-transitory computer readable medium of claim 6, wherein detecting, by the wearable device, the trigger event comprises:

analyzing, via one or more sensors of the wearable device, patient activity data to detect the trigger event.

10. The non-transitory computer readable medium of claim 6, wherein playing, by the wearable device, the instruction audio message to the patient of the wearable device comprises:

constructing the instruction audio message from a plurality of segments of pre-recorded audio.

11. A system comprising:

a processor; and a memory having programming instructions stored thereon, which, when executed by the processor, causes the system to perform operations comprising:

detecting a trigger event, wherein the trigger event indicates a type of measurement to take, wherein detecting the trigger event comprises:

determining a location of a user associated with the system based on beacon signals received from beacons in communication range of the system, and inferring a perceived state of the user based on the determined location of the user and motions detected by one or more sensors of the system;

based on the trigger event, selecting an instruction audio message corresponding to the type of measurement to be taken, the instruction audio message comprising instructions for how to conduct the type of measurement;

connecting to an appropriate measuring apparatus based on the type of measurement to be taken and the instruction audio message by identifying the appropriate measuring apparatus from among a plurality of possible measuring apparatuses and automatically pairing with the measuring apparatus using pre-configured identifiers, codes, or passwords to establish the connection without further user intervention;

playing the instruction audio message to a patient associated with the system; and receiving measurements from the appropriate measuring apparatus.

12. The system of claim 11, wherein detecting the trigger event comprises:

receiving a prompt from the patient associated with the system to record the type of measurement.

13. The system of claim 11, wherein detecting the trigger event comprises:

analyzing, via one or more sensors of the system, patient activity data to detect the trigger event.

14. The system of claim 11, wherein playing the instruction audio message to the patient associated with the system comprises:

constructing the instruction audio message from a plurality of segments of pre-recorded audio.

* * * * *